US00PP34400P2

(12) United States Plant Patent
Berryman

(10) Patent No.: US PP34,400 P2
(45) Date of Patent: Jul. 5, 2022

(54) CHERRY TREE NAMED "B1218"

(50) Latin Name: *Prunus avium*
Varietal Denomination: B1218

(71) Applicant: C. Richard Berryman, Zillah, WA (US)

(72) Inventor: C. Richard Berryman, Zillah, WA (US)

( * ) Notice: Subject to any disclaimer, the term of this patent is extended or adjusted under 35 U.S.C. 154(b) by 0 days.

(21) Appl. No.: 17/300,351

(22) Filed: May 21, 2021

(51) Int. Cl.
*A01H 5/08* (2018.01)
*A01H 6/74* (2018.01)

(52) U.S. Cl.
USPC ..... Plt./181

(58) Field of Classification Search
USPC ..... Plt./181
See application file for complete search history.

*Primary Examiner* — Annette H Para
(74) *Attorney, Agent, or Firm* — Svendsen Legal, LLC

(57) ABSTRACT

A new and distinct sweet cherry tree (*Prunus avium*) named 'B1218' is disclosed. 'B1218' is characterized by early maturing, and a generally heart-shaped fruit that is dark in color.

6 Drawing Sheets

Genus and species: *Prunus avium.*
Variety denomination: 'B1218'.

STATEMENT REGARDING FEDERALLY SPONSORED RESEARCH OR DEVELOPMENT

None

BACKGROUND AND ORIGIN OF THE NEW VARIETY

The new cherry cultivar that has been given the variety denomination 'B1218', was discovered in 2013 by inventor, as a whole tree cherry in an established orchard bloc of "Santina™" cultivar of cherry tree (not patented), on 'Giesla 6' rootstock (commonly referred to as 'G6') in a cultivated orchard, which was planted in 2010 and located at Zillah, Wash. The discovered mother tree of the naturally occurring sport 'B1218' is of unknown parentage, but assumed to be the 'Santina' cultivar.

Although the fruit of the 'B1218' mother tree was similar in color and shape to fruit from the 'Santina', the fruit on the 'B1218' mother tree matured five days to seven days after the 'Santina' cultivar's fruit. In 2016 this mother tree was genetically typed by the Foundation Plant Services of the University of California Davis, and discovered to be genetically different from 'Santina' and the forty-four other sweet cherry varieties on file. Second generation trees were grafted on 'Giesla 12' rootstock (commonly referred to as 'G12'), and planted in 2017. Throughout several generations of asexual propagation, 'B1218' has been observed to retain its distinctive characteristics and to remain true to type.

SUMMARY OF THE NEW VARIETY

The present invention relates to a new a distinct variety of cherry tree *Prunus avium*, which has been given the variety denomination 'B1218'. Specifically, 'B1218' is different from the "Santina™" cultivar of cherry tree (not patented) in that the bloom and the harvest maturity date of the 'B1218' is 5 days to 7 days later than the 'Santina' cultivar. Tree shape and bark of 'B1218' is similar to that of 'Santina'. Most importantly, the genetic profile of 'B1218' does not match 'Santina', nor does it match other known sweet cherry genetic profiles. Fruit skin and flesh color is dark mahogany of 'B1218', as is 'Santina', but the fruit at harvest maturity of 'B1218' is firmer and sweeter than 'Santana' and has a slightly less acid level on average. Second generation trees of 'B1218' exhibit fruit identical that of the 'B1218' mother tree.

COMPARISON OF 'B1218' TO COMARISON CULTIVAR

Table 1., below, sets forth some of the distinguishing characteristics of 'B1218' as compared the 'Santina' cultivar, as a closely comparable cultivar. Firmness ratings listed in Table 1. were measured using a 'Firm Tech 2' brand of firmness tester, and the listed ratings are in milligrams needed to depress 1 millimeter. Measurements were taken at the same packing run date, as listed.

TABLE 1

| Cherry | Harvest Date | Ave. Firmness | pH | ° Brix | Run Date |
|---|---|---|---|---|---|
| 'B1218' | Jun. 14, 2020 | 287 | 4.3 | 20.2 | Jul. 6, 2020 |
| 'Santina' | Jun. 18, 2020 | 254 | 4.1 | 15.3 | Jul. 6, 2020 |

BRIEF DESCRIPTION OF THE PHOTOGRAPHS

Figure 1:
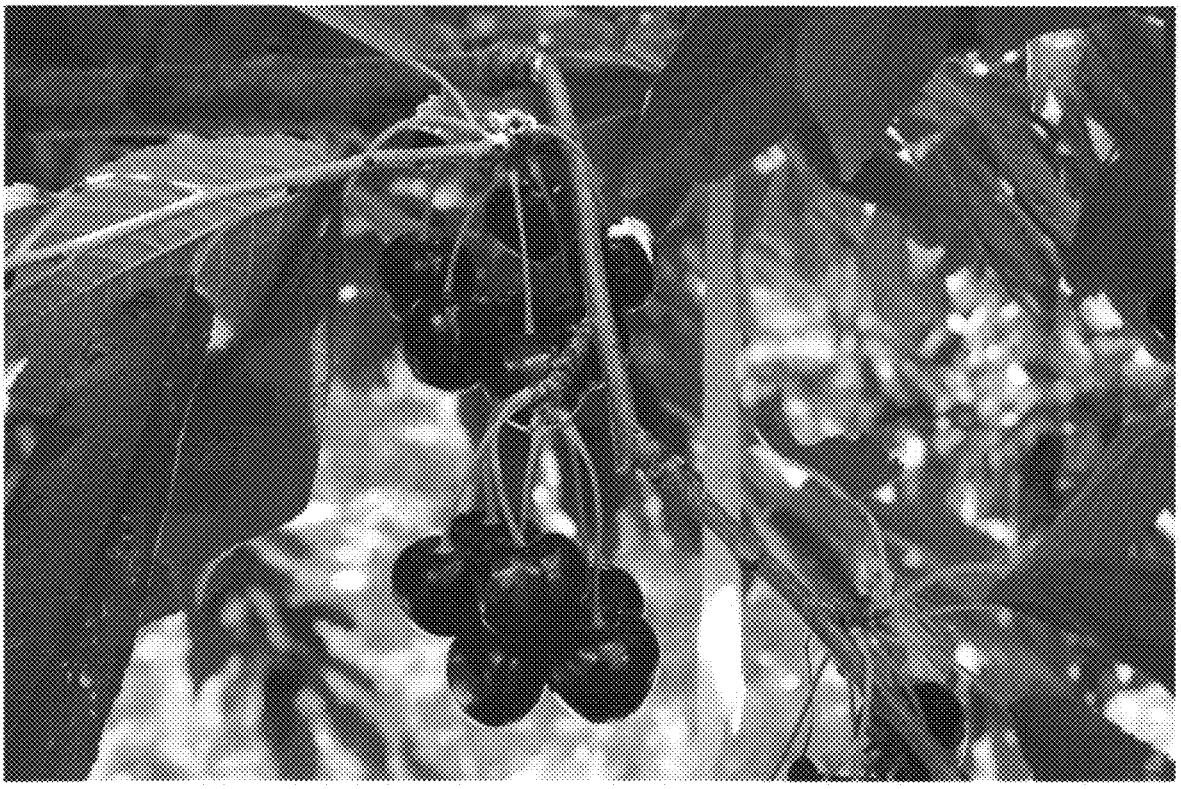
FIG. 1 is a color photograph that illustrates mature fruit clusters on a 'B1218' mother tree.
Figure 2:
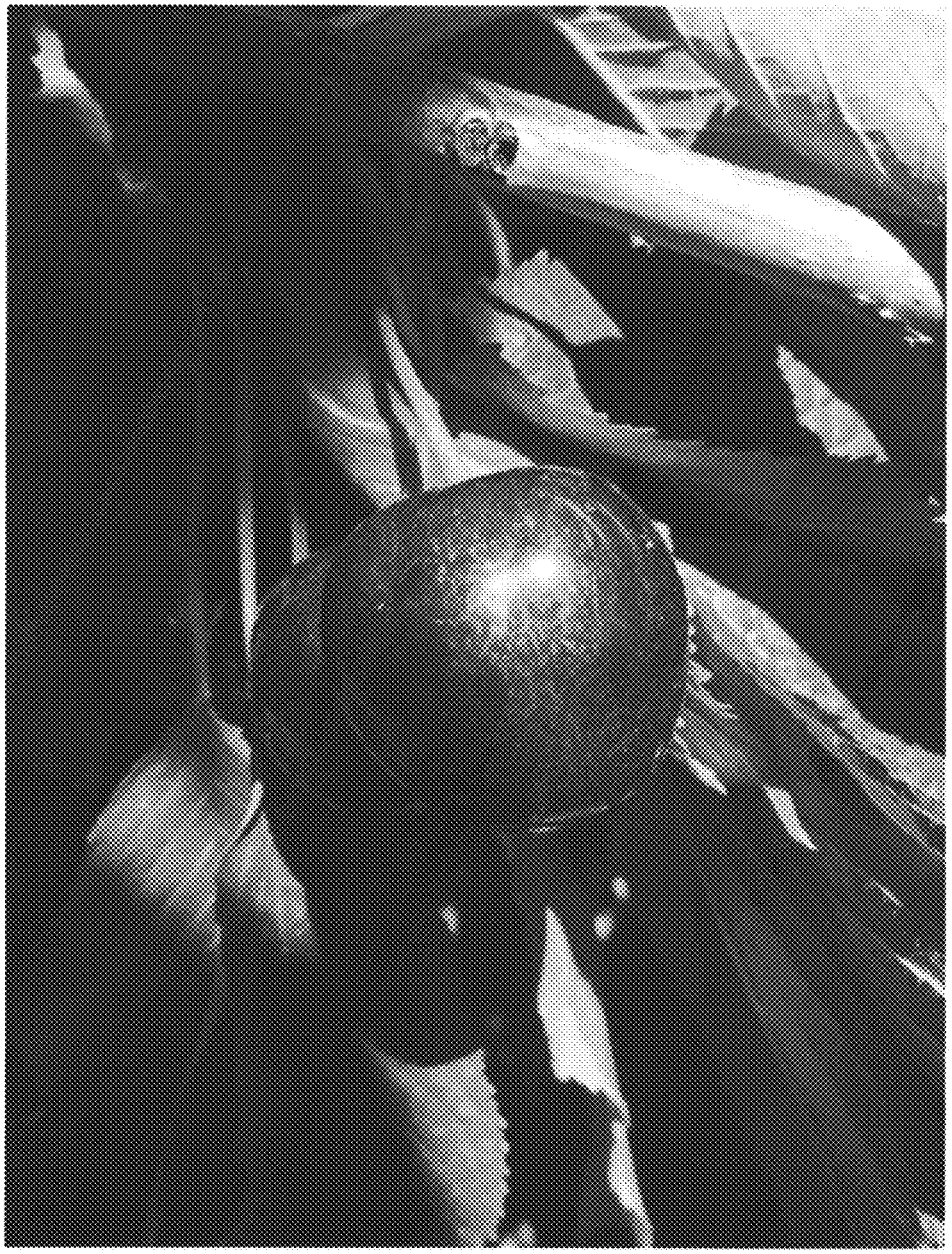
FIG. 2 is a color photograph that illustrates a near mature fruit cluster on the 'B1218' mother tree.
Figure 3:
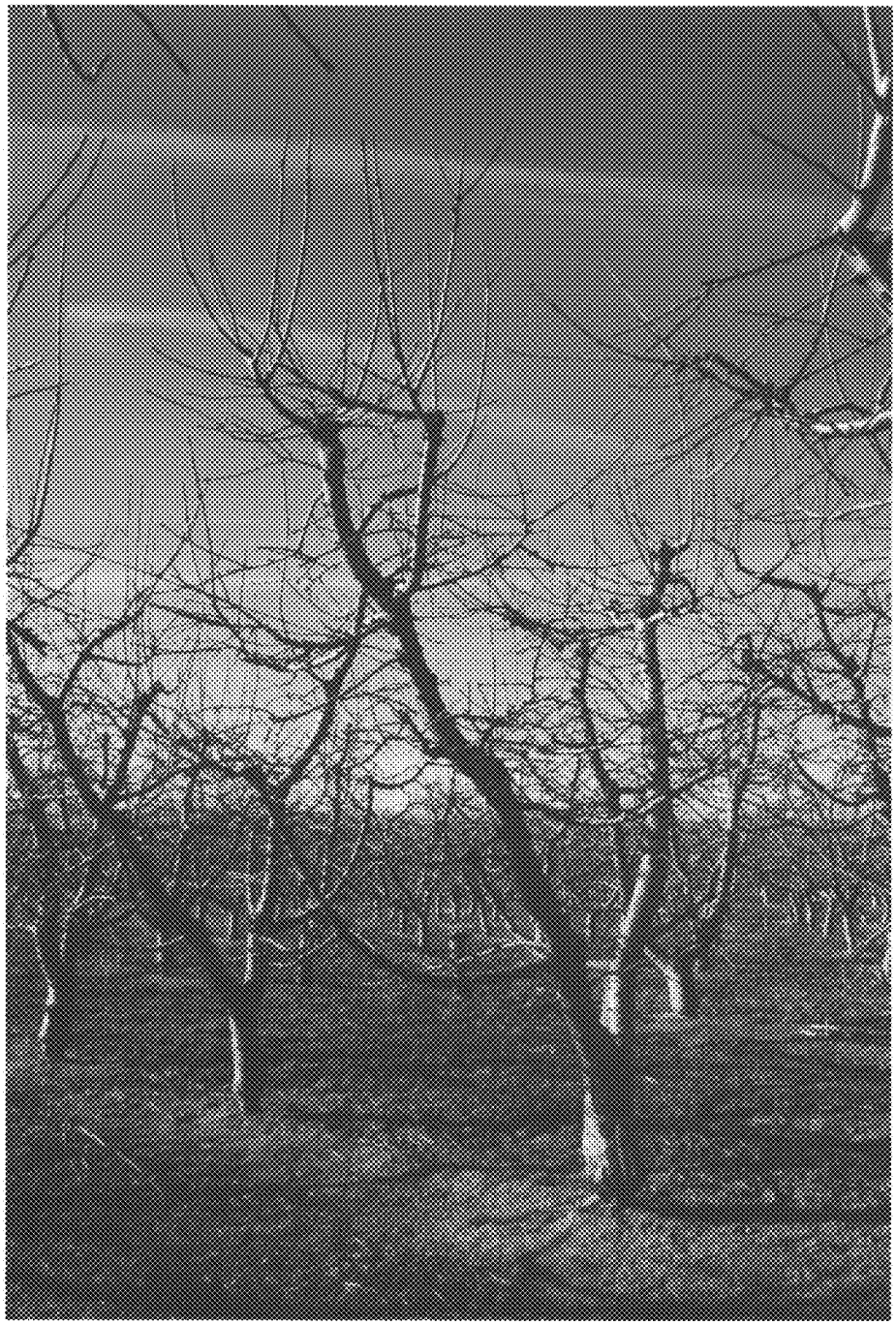
FIG. 3 is a color photograph that illustrates a dormant of the 'B1218' mother tree.
Figure 4:
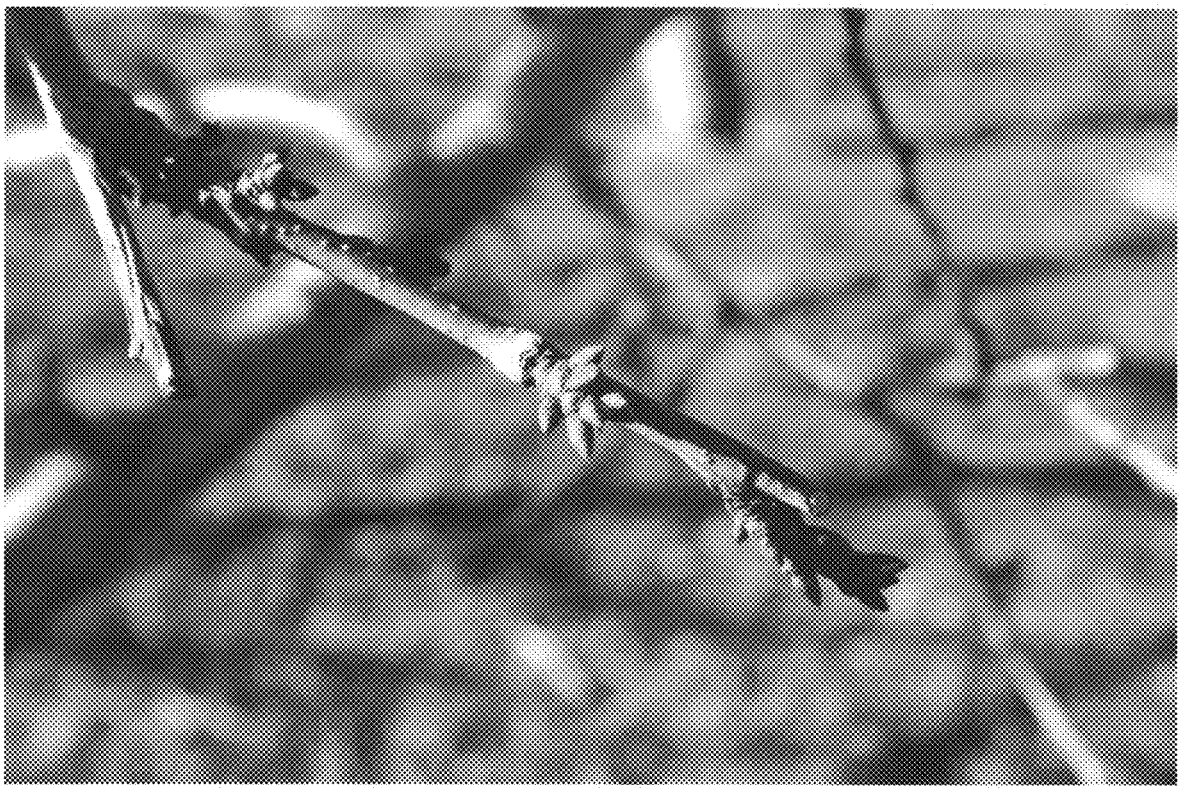
FIG. 4 is a color photograph that illustrates dormant fruiting bud development on the 'B1218' mother tree.
Figure 5:
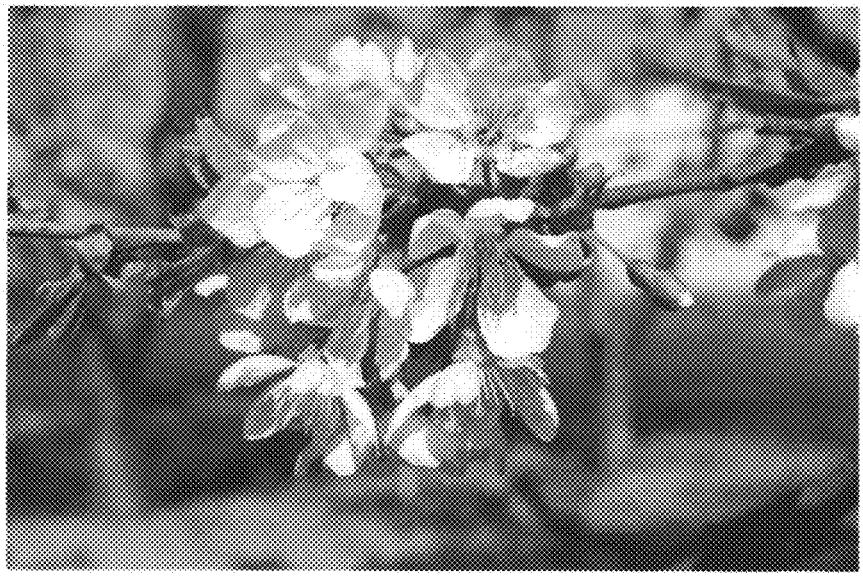
FIG. 5 is a color photograph that illustrates blossoms of the 'B1218' mother tree at full bloom.
Figure 6:
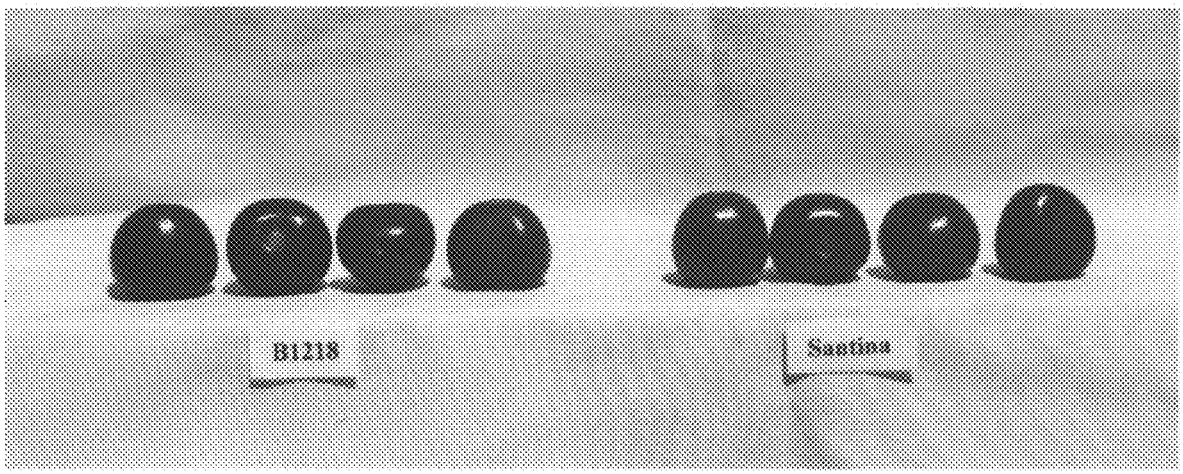
FIG. 6 is a color photograph that illustrates mature fruit of the 'B1218' and comparison mature fruit of the 'Santina' cultivar.

The colors of these photographic illustrations may vary with lighting conditions and, therefore, color characteristics of this new variety should be determined with reference to the observations described herein, rather than from these illustrations alone.

DETAILED BOTANICAL DESCRIPTION

The following description is based on observations made during the 2019-2020 growing seasons at Zillah, Wash. It should be understood that the characteristics described will vary somewhat depending upon cultural practices and climatic conditions, and can vary with location and season. Quantified measurements are expressed as an average of measurements taken from a number of individual trees of the new variety. The age of the trees observed at the time of this detailed botanical description was nine years since planting. The measurements of any individual tree or any group of trees of the new variety may vary from the stated average. All color references herein are based on The 2001 Royal Horticultural Society Colour Chart ($4^{th}$ edition).

Tree:

*Size*.—For observed age and rootstock, considered moderate at approximately 21 feet (6.4 m) in height, and 21 inches (53.3 cm) in diameter.

*Vigor*.—Considered moderate.

*Branching habit*.—Spreading.

*Density*.—Considered medium.

*Form*.—Open vase (as trained).

*Hardiness*.—Considered to be of normal hardiness for region.

*Production*.—Considered very good in precocity with an approximate yield of 9.5 tons to 10.0 tons per acre.

*Bearing*.—Annual.

Trunk (as measured at harvest maturity):

*Size*.—Circumference at 30 cm above ground is 69 cm.

*Bark texture*.—Considered as rough.

*Bark color*.—From the greyed-purple group N186A.

*Lenticels*.—Prominent with a horizontal orientation, with the number of lenticels averaging 13 lenticels per 9 square centimeter area, and with color from greyed-purple group 187B.

*Lenticels length*.—Ranges from 10.5 mm to 26.9 mm with an observed average of 18.0 mm.

*Lenticels width*.—Ranges from 2.6 mm to 4.9 mm with an average of 3.8 mm.

Branches (as measured at harvest maturity):

*Scaffold branches*.—Texture — Mostly smooth. Size — Circumference (measured 15 cm beyond trunk union) ranges from 44 cm to 55 cm with an average of 49.5 cm. Angles (as trained) range from 30 degrees to 45 degrees upward from horizontal. Color — From the greyed-purple group N186C. Lenticels — Numerous; averaging 18 per 9 square cm. Length ranges from 8.9 mm to 11.2 mm with an average of 10.1 mm; width ranges from 1.4 mm to 1.9 mm with an average of 1.7 mm; center color is from the greyed-orange group N167B; and outer margin color from the greyed-purple group 187B.

*Second year fruiting branches*.—Texture — Smooth. Diameter — Ranges from 3.7 mm to 6.5 mm at mid-point of growth with an average of 4.9 mm. Color — From the greyed-orange group 177A. Lenticels — Moderate in number averaging 8 per running cm; flat in shape and range from 0.2 mm to 0.5 mm in diameter, width of 0.1 mm; and color from the orange-white group 159D.

*Current year branches*.—Texture — Smooth. Size — Length ranges from 24 cm to 55 cm with an average of 41.6 cm; and diameter ranges from 5.1 mm to 7.8 mm, with an average diameter of 5.8 mm at half-way point. Color — From the yellow-green group 145A. Internode length — Ranges from 2.7 cm to 3.7 cm with an average of 3.2 cm. Lenticels — Ranges from 6 to 15 per running cm; round and ranging from 6 lenticels to 15 lenticels per running cm, with a diameter of 0.25 mm to 0.6 mm; and color is from the yellow-white group 158D.

Flower buds (measured at full bud swell or as noted otherwise):

*Spur length*.—Ranges from 8.9 mm to 26.2 mm, with an average of 15.6 mm.

*Bud shape*.—Elliptical with acute tip.

*Number buds per fruiting spur*.—Ranges from 4 buds to 9 buds with an average of 6 buds per fruiting spur.

*Bud length*.—Dormant ranges from 5.9 mm to 8.4 mm, with an average of 7.4 mm. Full swell ranges from 8.0 mm to 105 mm, with an average of 9.7 mm.

*Bud diameter*.—Dormant ranges from 2.8 mm to 3.6 mm, with an average of 3.5 mm. Full swell ranges from 4.1 mm to 5.8 mm, with an average of 4.7 mm.

*Scale color*.—From the greyed-orange group 177A.

Leaves (measurements from midpoint of actively growing current season's growth at terminal set):

*Blade*.—Size — Length ranges from 15.1 cm to 19.8 cm and averages 16.9 cm; width ranges from 5.8 cm to 7.5 cm with an average of 6.5 cm; and thickness ranges from 0.14 cm to 0.20 cm with an average of 0.16 mm. Texture — Upper surface is smooth and leathery, lower surface is smooth with vein protruding above surface. Tip — Narrowly acute. Base — Rounded. Form/shape — lanceolate. Margin — Biserrate. Blade color — Upper surface from the yellow-green group 147A; and lower surface color from the yellow-green group 147B. Mid-vein — Diameter at mid-point ranges from 1.1 mm to 1.4 mm with an average of 1.3 mm; and color from the yellow-green group 145B.

*Petiole*.—Size — Averages 34.0 mm in length with a range of 30.2 mm to 39.4 mm; and diameter at mid-point averages 2.2 mm with a range of 2.0 mm to 2.4 mm. Color — Upper surface color from the greyed-orange group 166A; lower surface color from the yellow-green group 145B; and a groove with a depth of 0.1 mm to 0.3 mm runs the full length of upper surface. Glands — Present, and all within 10 mm of blade and mostly alternate, occasionally opposite; length ranges 2.3 mm to 5.0 mm with an average of 3.1 mm; width ranges from 1.6 mm to 2.2 mm with an average of 1.9 mm; with 1 gland to 3 glands per petiole, mostly 2 glands per petiole; and color from the greyed-red group 178B.

*Stipules*.—Size and Number — Mostly 0 in number, but occasionally 1 or 2 with spinney margins; length ranges from 13.4 mm to 15.6 mm with an average of 14.3 mm; width at mid-point ranges from 0.6 mm to 1.0 mm with an average of 0.8 mm. Color — At basal from the greyed-yellow group 161B, and at tips from the greyed-orange group 166A. Attitude: Moderate droop.

Flowers: Bloom stands out, with moderate droop.

*Observed first bloom*.—Apr. 7, 2020.

*Observed full bloom*.—Apr. 12, 2020 (with a three-year average of April 14).

*Size*.—Bloom diameter when fully open averages 33.5 mm with a range of 4.2 cm to 4.8 cm and is considered large.

*Bloom count*.—Ranges from 2 blossoms to 5 blossoms per bud, mostly 2 blossoms per bud.

*Petals*.—Five in number; color is from the white group 155D; average length is 20.2 mm with a range from 19.3 mm to 21.7 mm; average width is 14.6 mm with a range from 12.7 mm to 17.2 mm; and when fully open, petals are considered free and do not touch.

*Petal shape*.—More ovate than round; base is rounded; and apex is emarginate.

*Stamens*.—Filaments — Ranges from 38 to 42 in number, with an average of 39 filaments per bloom; length ranges from 6.0 mm to 11.4 mm with an average of 8.3 mm; and color is from the white group 155C; Anther — Globose in shape, with length ranging from 0.4 mm to 0.6 mm; and width ranging from 0.3 mm to 0.5 mm. Pollen — Abundant; with color from the greyed-orange group 170A.

*Carpel*.—Style — Length ranging from 11.2 to 12.4 mm, with an average of 11.7 mm; diameter at mid-point ranges from 0.5 mm to 0.6 mm; and color is from the yellow-green group 145B. Stigma — Clubbed and kidney in shape; with diameter ranging from 0.7 mm to 1.6 mm, with an average of 1.3 mm; and color from the yellow-green group 145B. Nectary color — Color is from the yellow-green group 144A.

*Sepals*.—Five in number; elliptical in shape and folded back, touching thalmus; length ranging from 5.8 mm to 8.2 mm, with an average of 6.7 mm; width ranging from 4.4 mm to 6.2 mm, with an average of 5.2 mm; and the color of both sides from the yellow-green group 144A.

*Peduncle*.—Length ranges from 15.0 mm to 25.1 mm, with an average of 21.3 mm; diameter ranges from 0.7 mm to 1.1 mm, with an average of 1.0 mm; and color is from the green group 137D.

*Thalmus*.—Depth ranges from 6.1 mm to 8.2 mm, with an average of 7.6 mm; width ranges from 4.5 mm to 5.9 mm, with an average of 5.1 mm; urn shaped; and color from the green group 143D.

Fruit:

*Maturity*.—Observed Harvest maturity Jun. 16, 2020.

*Quantity per cluster*.—1 fruit to 3 fruits per fruit cluster, mostly 2 fruits.

*Overall form*.—Considered uniform and more chordate than round. Backside flattened in area of suture.

*Base shape*.—Round with cavity.

*Cavity depth*.—Ranges from 2.9 mm to 3.9 mm with an average of 3.3 mm.

*Apex shape*.—Rounded with small russeted dot at tip that is 1.2 mm to 1.7 mm diameter; and with color from the grey-brown group N199C.

*Size*.—Apical diameter — Ranges from 25.0 mm to 29.5 mm, with an average of 27.3 mm. Axial side to side diameter — Ranges from 28.9 mm to 31.1 mm, with an average of 30.0 mm. Suture axial diameter — Ranges from 24.9 mm to 27.5 mm with an average of 26.4 mm.

*Suture*.—Indistinct to very light, located at back side apex end of fruit; width Ranges from 0.6 mm to 1.1 mm; and with depth of 0.1 mm (very shallow).

*Peduncle*.—Length ranges from 4.3 cm to 6.1 cm with an average of 5.0 cm; with a diameter at mid-point ranging from 1.1 mm to 1.6 mm, with an average of 1.4 mm; and color is from the yellow-green group 146B.

*Skin*.—Thickness — Considered thin, 0.23 mm to 0.27 mm. Texture — Surface is smooth. Tenacity — Light, peels easily. Tendency to crack — Resistant. Down — None observed. Color — Uniform, from the greyed-purple group 186B.

*Flesh*.—Color — From the greyed-purple group N166C. Surface of pit cavity color — From the greyed-purple group N186A. Texture — Mostly smooth. Fibers — Very light, nearly indistinct. Pit tenacity — Moderate. Ripens — Evenly. Flavor — Cherry like, moderate in intensity. Aroma — Very light to lacking in cherry smell. Eating quality — Excellent. Firm and sweet.

*Stone*.—Type — Light-cling type. Base to apex — Ranges from 12.3 mm to 13.3 mm with an average of 12.8 mm. Shoulder to shoulder — Ranges from 7.4 mm to 8.3 mm, with an average of 8.0 mm. Suture to suture — Ranges from 9.7 mm to 10.6 mm with an average of 10.2 mm. Form — Narrow elliptic. Base — Rounded. Apex — Rounded. Sides — Equal (uniform). Surface — Smooth. Ventral Edge — Suture is slightly raised 0.9 mm to 1.1 mm and is subtended by two low ridges converging basally and apically that averages 0.8 mm in height, and distance between ridges averages 4.7 mm. Color — From the orange-white group 159B. Tendency to split — None observed. Rain resistant.

*Kernel*.—Shape — Considered obtuse. Base — Rounded. Apex — Acute. Size — Length ranges from 6.8 mm to 7.7 mm, with an average of 7.2 mm; width ranges from 4.0 mm to 5.3 mm, with an average of 4.6 mm; and thickness ranges from 2.4 mm to 4.2 mm with an average of 3.3 mm. Color — From the yellow-white group 158D. Taste — Biter, almond like. Viability — 100% kernel development observed, and viable kernel germination unknown.

Pollination requirement: Self pollinating.

Genetics: The Foundation Plant Services of the University of California Davis, at Davis, Calif., performed a genetic analysis of 'B1218' and found that its profile did not match any of the forty-five cherry profiles in their database.

Use: Desert. Excellent eating quality and premium fresh market.

Resistance to insects and diseases: Susceptible to insects and diseases affecting cherries in the south central region of Washington State, where grown.

Shipping and storage quality: Very good to excellent in conventional refrigeration.

Variance in botanical details: Fruit of the 'B1218' variety is very uniform in size and shape from mother tree. Second generation trees of 'B1218' are uniform in all aspects. 'B1218' exhibits the herein above described characteristics as grown in Yakima County, in the south central region of Washington State. It is expected that differences may occur when grown in areas exhibiting different growing conditions.

What is claimed:

1. A new and distinct variety of Cherry Tree as illustrated and described herein.

* * * * *